United States Patent
Sakano

[19]

[11] Patent Number: 5,922,012
[45] Date of Patent: Jul. 13, 1999

[54] LOW-FREQUENCY ELECTROTHERAPEUTIC DEVICE HAVING THREE OR MORE ELECTRODES FOR GENERATING FLEXIBLE STIMULATION PATTERNS

[75] Inventor: Kazuhito Sakano, Funahashi-mura, Japan

[73] Assignee: Toyo Sangyo Co., Ltd., Japan

[21] Appl. No.: 08/690,893

[22] Filed: Aug. 1, 1996

Related U.S. Application Data

[30] Foreign Application Priority Data

Aug. 4, 1995 [JP] Japan ................................ 7-199525

[51] Int. Cl.⁶ .............................. A61N 1/04; A61N 1/32
[52] U.S. Cl. .............................. 607/46; 607/72; 607/145; 607/148; 607/149; 607/151; 607/152
[58] Field of Search ..................... 607/145, 148, 607/149, 151, 152, 72, 74, 46, 63

[56] References Cited

U.S. PATENT DOCUMENTS

| | | | |
|---|---|---|---|
| 4,033,356 | 7/1977 | Hara | 607/152 |
| 4,254,776 | 3/1981 | Tanie et al. | 607/63 |
| 4,381,789 | 5/1983 | Naser et al. | 607/152 |
| 4,510,939 | 4/1985 | Brewman et al. | 607/145 |
| 4,875,484 | 10/1989 | Anzai et al. | 607/46 |
| 4,926,864 | 5/1990 | Dufresne et al. | 607/72 |
| 5,257,623 | 11/1993 | Karasev et al. | 607/27 |
| 5,498,235 | 3/1996 | Flower | 607/152 |
| 5,578,065 | 11/1996 | Hattori et al. | 607/72 |
| 5,584,865 | 12/1996 | Hirschberg et al. | 607/5 |
| 5,695,459 | 12/1997 | Meguro | 607/72 |

FOREIGN PATENT DOCUMENTS

| | | | |
|---|---|---|---|
| 62-137067 | 6/1987 | Japan | A61N 1/04 |
| 63-192459 | 8/1988 | Japan | A61N 1/32 |
| 63-257577 | 10/1988 | Japan | A61N 1/32 |

*Primary Examiner*—William E. Kamm
*Assistant Examiner*—Carl H. Layno
*Attorney, Agent, or Firm*—Michaelson & Wallace; Peter L. Michaelson; John C. Pokotylo

[57] ABSTRACT

A low-frequency electrotherapeutic device can overcome problems ascribable to tolerance in neural response and problems ascribable to accumulation of electric charge in a living body, thereby affording a comfortable massaging effect. Each electrode can be designated as a different electrode or as an indifferent electrode by a controller. Electrodes do not assume a fixed paired structure, and the path of stimulating electric current is changed at predetermined intervals by scanning electrodes serving as different electrodes. The path of an electric current flowing on the skin of a living body can be changed in various ways, the number of which corresponds to the number of paths connecting the electrodes. Consequently, it becomes possible to freely select a desired electric current path or a desired combination of electrodes in accordance with a program stored in a control section (CPU) incorporated in the controller. Also, it becomes possible to automatically change the combination at predetermined intervals. As a result, the apparent electrode position on the base film sheet changes, so that the stimulating position varies.

20 Claims, 9 Drawing Sheets

FIG. 2
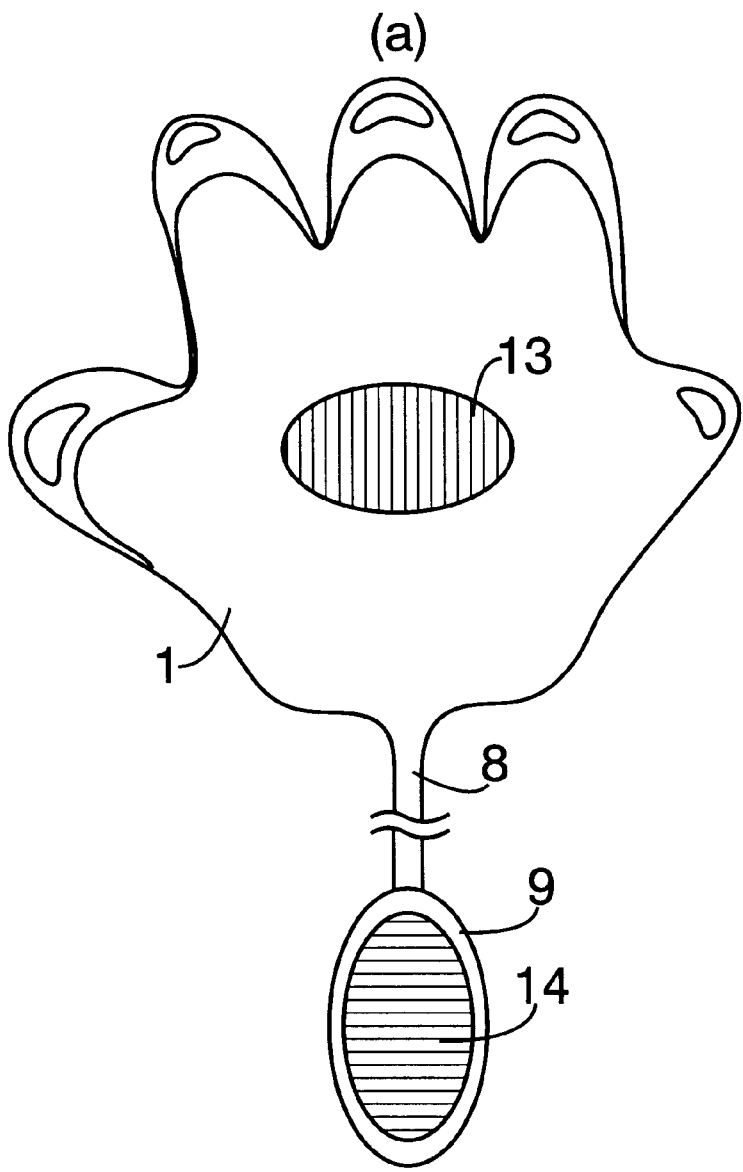
(a)
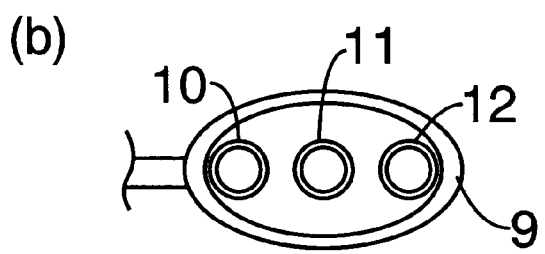
(b)
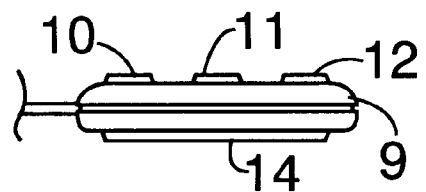

LOW-FREQUENCY ELECTROTHERAPEUTIC DEVICE HAVING THREE OR MORE ELECTRODES FOR GENERATING FLEXIBLE STIMULATION PATTERNS

BACKGROUND OF THE INVENTION

1. Field of the Invention

The present invention relates to a low-frequency electrotherapeutic device.

2. Description of the Related Art

Conventional low-frequency electrotherapeutic devices are generally of a structure in which there is provided a pair comprising a different electrode and an indifferent electrode, with the paired electrodes being used alone as electrodes for medical treatment. Exceptionally, in Japanese Patent Application Laid-Open No. 63-192459, there is proposed a low-frequency electrotherapeutic device wherein five pairs are provided, each pair comprising a dot-like positive electrode 101 and an annular negative electrode 102, as shown in FIG. 7. In this low-frequency electrotherapeutic device, although five pairs of different electrodes and indifferent electrodes are arranged in a rectangular shape, the structure thereof can be regarded as essentially using only a single pair comprising a different electrode and an indifferent electrode. In Japanese Patent Application Laid-Open No. 63-257577, there is proposed a low-frequency electrotherapeutic device having a different electrode 103 and an indifferent electrode 104 which are concentric with each other, as shown in FIG. 8. The structure of this low-frequency electrotherapeutic device can also be regarded as including only a pair comprising a different electrode and an indifferent electrode. Further, in Japanese Patent Application Laid-Open No. 62-137067 is proposed a low-frequency electrotherapeutic device wherein three electrodes are arranged in parallel, with the central electrode being used as an indifferent electrode while the electrodes located at either side of the central electrode are used as different electrodes which are simultaneously supplied with an electric current. However, even in the low-frequency electrotherapeutic device described in Japanese Patent Application Laid-Open No. 62-137067, the two different electrodes are electrified simultaneously; hence the structure of the device can also be regarded as essentially using a single pair comprising a different electrode and an indifferent electrode.

Thus, each of the conventional low-frequency electrotherapeutic devices referred to above consists essentially of a single pair comprising a different electrode and an indifferent electrode, wherein the positional relationship between the different electrode and the indifferent electrode is fixed. An electrical circuit, through which a stimulating current flows from the positive electrode to the negative electrode, is always formed at a limited position of the skin of a living body; that is, stimulation is repeated at the same position adjoining the skin of the living body. Continuing the electric stimulation at such a limited position on the living body skin is discomforting to the living body and makes the stimulation less effective due to habituation.

The above-described problems in relation to the stimulating current being applied at the same position of the body occur even in the structure wherein a different electrode and an indifferent electrode are connected through lead wires to a controller so as to allow the distance between both electrodes on a living body to be freely changed, or even in the structure having five pairs, each pair comprising a different electrode and an indifferent electrode, such as that shown in FIG. 7, because once the different electrode(s) and the indifferent electrode(s) are attached to a living body, their positional relation becomes fixed. Therefore, the foregoing problems have been solved by neither the low-frequency electrotherapeutic devices presently available in the market nor those proposed in the past.

In efforts to solve the above-mentioned problem, there have heretofore been conducted studies regarding the method of varying the voltage waveform outputted from a different electrode so as to thereby automatically change the type of stimulation in the range of at least three patterns and at most seven or eight patterns, as shown in FIGS. 9 and 10. Sine wave F, square wave G and exponential wave H are composite variations of group waveform I in all. These are considered to be a factor of time (both fast and slow K) and considered to be variations in periods T1–T4 in FIG. 9. The factor of strength M is considered to be variations in voltages V1–V4 in FIG. 9 producing different strength outputs.

However, even if the width and magnitude of each pulse in the pattern are changed shown in FIG. 9, or the stimulation pattern is changed as in FIG. 10, the human becomes less sensitive to such stimulating current. That is, any person, in his or her neural response, exhibits a tolerance against stimulation repeated at the same position on his or her body. As a result, no matter how the type of stimulation may be changed, the person loses sensitivity in discriminating between stimulation with respect to the type and strength. This phenomenon is well known within the field of physiology. Consequently, even with stimulation pattern changed as in FIG. 10, for example, even if a weak stimulation is given to a human just after a strong stimulation (such as voltage V2 after V1 or voltage V4 after V3 in FIG. 9), the human can no longer sense it as stimulation. The longer continued the stimulation, the more marked this tendency.

Thus, according to the electrode structure of the conventional low-frequency electrotherapeutic devices wherein the positional relationship between a different electrode and an indifferent electrode is fixed, a patient being treated by the device exhibits a tolerance in his or her neural response, with the result that the effects of treatment for diseases of the nervous system such as neuralgia and palsy of the peripheral nerve, which treatment effects are clearly mentioned to be provided by the electrotherapeutic devices, become deteriorated with the lapse of working time of the devices.

In addition to the above problem relating to the tolerance in neural response, there also has been the problem that an electric charge is accumulated in the human living body tissue due to the electric current outputted from the low-frequency electrotherapeutic devices. More particularly, as long as the positional relation between the different electrode and the indifferent electrode within each such low-frequency electrotherapeutic device remains fixed, the path of electric current also becomes fixed and the aforesaid accumulation of electric charge in the living body also occurs at the same position. As a result, the waveform of the output voltage from the different electrode is greatly distorted; therefore, a stimulating electric current has difficulty in flowing through the living body and the patient undergoing medical treatment feels stimulation only to an extremely slight degree.

Due to the aforesaid accumulation of electric charge in the living body caused by continued stimulation at the same position of the living body, effects of massage such as the recovery from fatigue and the promotion of blood circulation are also deteriorated.

Even apart from the problems caused by the tolerance in neural response and the problems caused by accumulation of electric charge in the living body, the repeated electric stimulation at the same position of the living body causes discomfort.

SUMMARY OF THE INVENTION

The present invention has been accomplished in view of the above-mentioned problems of the prior art techniques and it is the object of the present invention to provide a low-frequency electrotherapeutic device that solves the problems caused by tolerance in neural response as well as those caused by accumulation of electric charge in a living body, thereby attaining a comfortable massaging effect.

In order to achieve the above-mentioned object, the present invention provides a low-frequency electrotherapeutic device, which comprises a step-up pulse circuit, a control section (CPU) for controlling the step-up pulse circuit, a power source for supplying electric power to both the step-up pulse circuit and the control section (CPU), (also referred to as the controller) an output circuit connected to the step-up pulse circuit, the output circuit being controlled by the control section (CPU), and electrodes connected to the output circuit.

Three or more of the electrodes are provided, and each of the electrodes is freely designated as a different electrode or as an indifferent electrode.

The present invention provides another low-frequency electrotherapeutic device, which comprises a step-up pulse circuit, a control section(CPU) for controlling the step-up pulse circuit, a power source for supplying electric power to both the step-up pulse circuit and the control section (CPU), an output circuit connected to the step-up pulse circuit, the output circuit being controlled by the control section(CPU), and electrodes connected to the output circuit. Three or more of the electrodes are provided, and each of the electrodes is freely designated as a different electrode or as an indifferent electrode. The arrangement of the thus-designated different or indifferent electrodes is not a fixed paired arrangement.

The present invention provides still another low-frequency electrotherapeutic device, which comprises a step-up pulse circuit, a control section(CPU) for controlling the step-up pulse circuit, a power source for supplying electric power to both the step-up pulse circuit and the control section (CPU), an output circuit connected to the set-up pulse circuit, the output circuit being controlled by the control section (CPU), and electrodes connected to the output circuit. Three or more of the electrodes are provided, and each of the electrodes is freely designated as a different electrode or as an indifferent electrode, wherein a desired combination of different and indifferent electrodes is formed. The thus-designated different and indifferent electrodes from a paired arrangement.

Accordingly, each of the three or more electrodes can be used freely as a different electrode or as an indifferent electrode. Since it is possible to designate a desired different-indifferent electrode combination, a change-over between different and indifferent electrodes can be freely made in accordance with a program stored in the controller, thus making it possible to automatically change-over from one stimulating position for a living body to another, thereby rendering the operations performed by the low-frequency electrotherapeutic device as similar as possible to "kneading," "rubbing," and "tapping" operations performed by a human.

Preferably, the three or more electrodes operate independently by controlling the output circuit.

Preferably, the three or more electrodes comprise a non-linear arrangement.

Preferably, the three or more electrodes comprise an arrangement along a curved line whose curvature is smaller than infinity.

Preferably, there is further provided a function of changing or switching means to change an electric current path between a different electrode(s) and an indifferent electrode (s).

Preferably, there is provided a function of changing or switching means to change an electric current path between a different electrode(s) and an indifferent electrode(s) and the output circuit drives a scanning device to scan a plurality of electrodes serving as different electrodes or indifferent electrodes.

Preferably, a different electrode(s) and an indifferent electrode(s) are independently designated by a controller.

Preferably, the electrodes are disposed at positions closely similar to the positions of the human fingers and palm.

Preferably, the electrodes are arranged on a single sheet.

Preferably, the electrodes are arranged on each of the front and back surfaces of the aforesaid single sheet.

Preferably, the aforesaid single sheet has cuts so as to easily fit a curved surface of a living body when attached to the living body.

Thus, by scanning the electrodes in accordance with the program stored in the controller, it is possible to change the stimulating positions while the low-frequency electrotherapeutic device remains attached to the human skin. Therefore, it becomes unnecessary to detach electrically conductive adhesive pads from the human skin and to attach them at different locations whenever the stimulating position is changed. This greatly prolongs the service life of the electrically conductive adhesive pads.

Shifting the stimulating positions, which is effected by the above-described construction of the low-frequency electrotherapeutic device of the present invention, is very effective in preventing the nervous system from developing tolerance. More particularly, in the conventional low-frequency electrotherapeutic device, stimulation is repeated at a fixed limited position, resulting in the creation of tolerance. By contrast, in the low-frequency electrotherapeutic device of the present invention, none of the electrodes is fixedly used as a different electrode or as an indifferent electrode; that is, the electrodes for stimulation are controlled in accordance with the controller program, such that the stimulating position shifts horizontally on the living body to which the device is applied, as if the stimulating position were free-running. As a result, the problems involved in the conventional low-frequency electrotherapeutic devices can be avoided. By suppressing the development of tolerance on the part of the nervous system it becomes possible to make a more effective treatment for diseases related to the nervous system such as neuralgia, muscle pain, and palsy of the peripheral nerve.

Moreover, in the low-frequency electrotherapeutic device of the present invention, since the accumulation of electric charge in a living body is suppressed by shifting the stimulating positions, thereby preventing the distortion of the waveform of the voltage outputted from each different electrode, the effect of electric stimulation which the patient can feel is not attenuated even upon continued use of the device.

The medical treatment provided by the low-frequency electrotherapeutic device of the present invention can also afford an outstanding massaging effect and it is evident that a massaging operation involving a shift of the stimulating positions is more effective in the recovery from fatigue and in the promotion of blood circulation.

In addition, shifting the stimulating positions in the above-described construction of the low-frequency electrotherapeutic device of the present invention is extremely effective in attaining power savings for the low-frequency electrotherapeutic device; that is, in suppressing the power consumption of the power source (battery) and prolonging the battery life.

More specifically, according to the conventional low-frequency medical treatment method wherein stimulation is repeated at the same positions, the strength of stimulation must be increased as the patient becomes accustomed to the stimulation, and a larger amount of electric power is consumed due to increasing the strength of stimulation. In contrast therewith, in the low-frequency electrotherapeutic device of the present invention, the positions of different electrodes and indifferent electrodes are not fixed and the stimulating positions are changed, so that the development of tolerance (habituation) is prevented and the expected effect can be attained even without specially increasing the stimulation voltage.

Preferably, an end portion of the aforesaid single sheet is extended, and the controller is connected to the extended portion, the electrodes being controlled by the controller.

Preferably, the controller can be easily attached to and detached from the single sheet through magic tape provided on the single sheet.

Preferably, there is provided on the surface of each electrode an adhesive pad having a bonding surface which has stickiness for the skin.

Preferably, the aforesaid adhesive pad is impregnated with a medicine.

Accordingly, a controller is positioned at an extended end portion of the sheet-like body of the electrotherapeutic device, and the sheet-like body is inserted into the central portion of the controller. Therefore, when such a low-frequency electrotherapeutic device is attached to, for example, the shoulder of a patient, the controller assumes a pendent state like that of a pendant, but no lead wire is used. A tail end portion formed by extending the base film of the electrotherapeutic device is used to support the controller. There is no fear of wire being an obstacle and causing entanglement as is the case with a remote control type using a lead wire. There is also an elimination in relation to inconvenience of the operation of the controller in which the operation cannot be visually checked, as is the case where the controller is fixed onto the body of a low-frequency electrotherapeutic device with a snap button or the like, with an electric current being supplied from the snap button. Thus, it is easy to operate the controller of the present invention, and the controller can be easily attached to the extending portion of the base film.

BRIEF DESCRIPTION OF THE DRAWINGS

The invention will be more readily understood by reference to the following detailed description taken in conjunction with the accompanying drawings wherein:

FIG. 2(a) is a back view of the low-frequency electrotherapeutic device of the embodiment illustrated in FIG. 1;

FIG. 2(b) is a view as seen in the direction of arrow B in FIG. 1(a);

DESCRIPTION OF PREFERRED EMBODIMENTS

Embodiments of the present invention will now be described with reference to the accompanying drawings.

Figure 1:
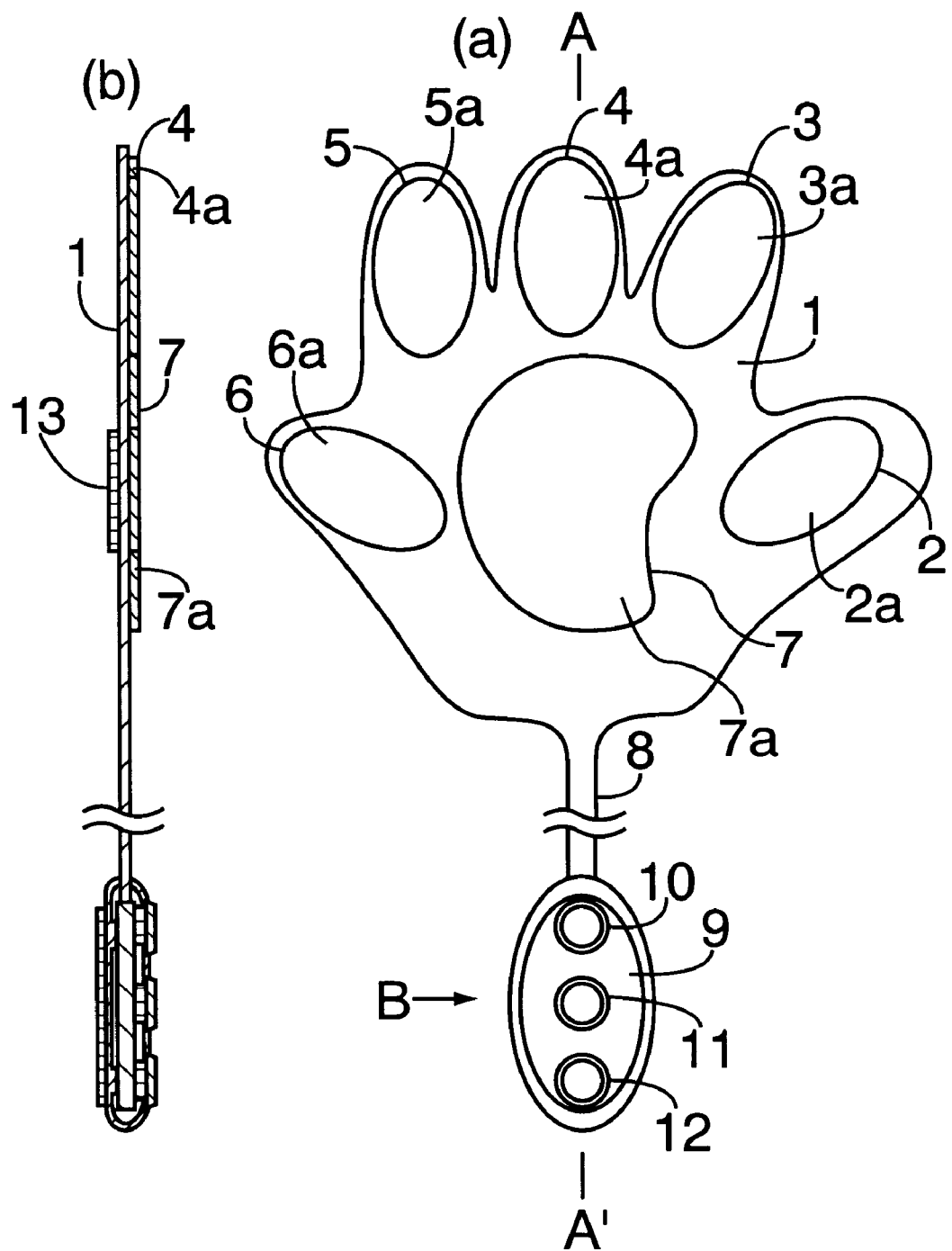
FIG. 1(a) is a surface view of a low-frequency electrotherapeutic device according to an embodiment of the present invention, showing a portion corresponding to the palm of the hand.
FIG. 1(b) is a sectional view taken along line A–A' in FIG. 1(a)

FIG. 1(a) is a surface view of a low-frequency electrotherapeutic device according to an embodiment of the present invention, showing a portion corresponding to the palm of the hand, and FIG. 1(b) is a sectional view taken along line A–A' in FIG. 1(a). In FIG. 1, reference numeral 1 denotes a base film sheet of the device body, which sheet is, for example, a vinyl chloride sheet. Electrodes 2, 3, 4, 5 and 6 have medicinal adhesive pads 2a, 3a, 4a, 5a and 6a, respectively, comprise a non-linear arrangement on the surface a of the base film sheet 1. In other words, the electrodes 2, 3, 4, 5 and 6 comprise an arrangement along a curved line having a curvature smaller than infinity.

In FIGS. 1(a) and 1(b), numeral 7 denotes a central electrode having a medicinal adhesive pad 7a, the central electrode 7 being disposed nearly centrally of the base film sheet 1.

One end of a pendant cable 8 is attached to the base film sheet 1, and to the opposite end thereof is connected a pendant type controller 9. The pendant type controller 9 is provided with operating buttons 10, 11 and 12. The pendant type controller 9 is attached to an extended end portion of the base film sheet 1, and the base film sheet 1 is inserted into the central portion of the controller. Among the operating buttons 10, 11 and 12, the operating buttons 10 and 12 are used for setting the voltage high or low, while the operating button 11 is used to select the type of stimulation induced by a low frequency pulses, that is, to perform mode selection.

FIG. 2(a) is a back view of the low-frequency electrotherapeutic device illustrated in FIG. 1, showing a portion corresponding to the palm of the hand, and FIG. 2(b) is a view as seen in the direction of arrow B in FIG. 1(a). Further, FIG. 3(a) is a back view of the low-frequency electrotherapeutic device illustrated in FIG. 1, showing the controller 9 held at a predetermined position on the base film sheet 1, and FIG. 3(b) is a view as seen in the direction of arrow A in FIG. 3(a).

As shown in FIG. 2, a magic tape 13 is affixed to a nearly central position of the base film sheet 1, and a magic tape 14 is affixed to the back side of the controller 9, namely, the side opposite the side where the operating buttons 10, 11 and 12 are mounted. Therefore, as shown in FIGS. 3(a) and 3(b), when the low-frequency electrotherapeutic device of the embodiment illustrated in FIG. 1 to 3 is not in use, the controller 9 can be held onto the base film sheet 1 by joining the magic tape 13 on the controller 9 with the magic tape 14 on the base film sheet.

Figure 3:
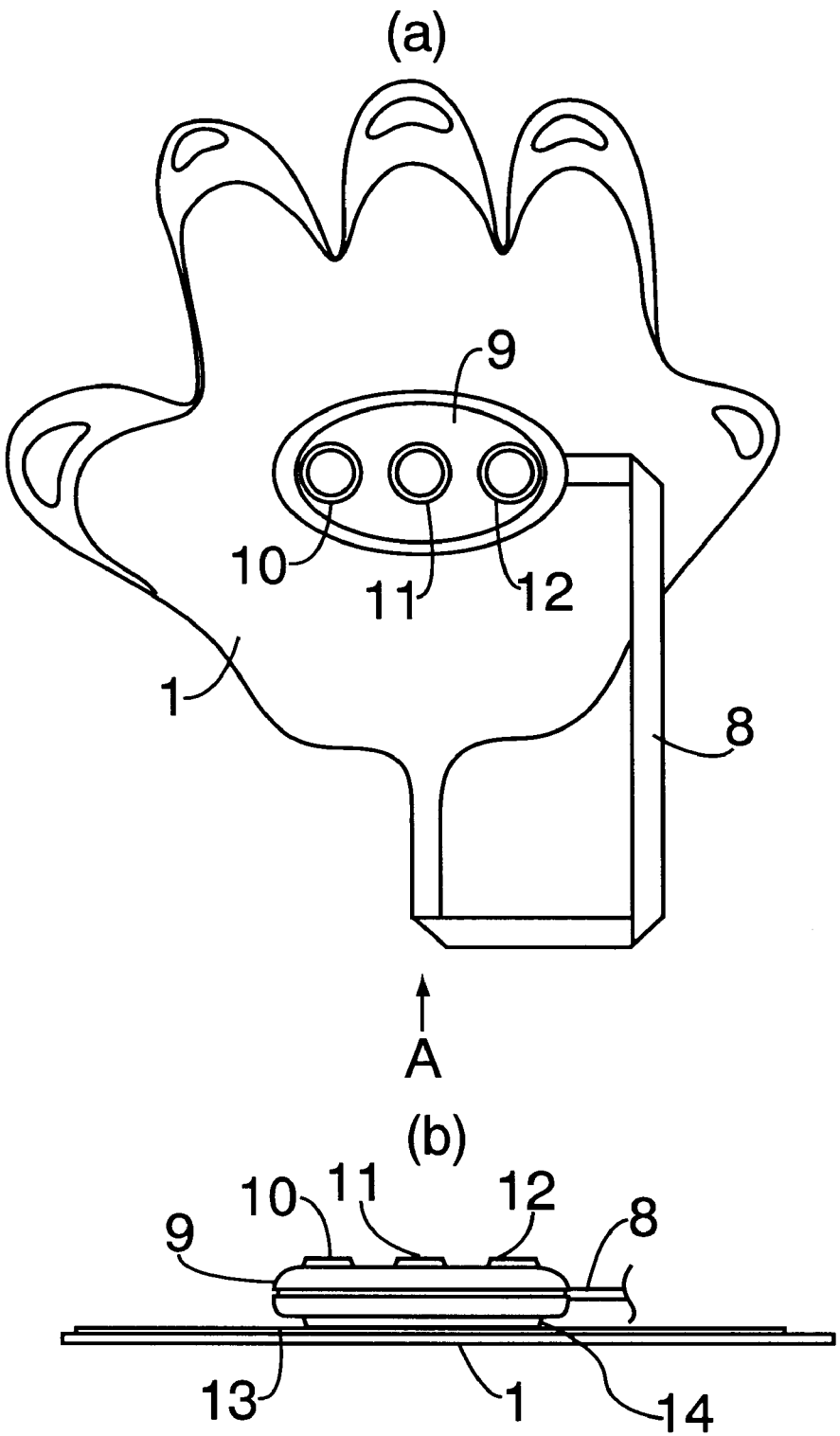
FIG. 3(a) is a back view of the low-frequency electrotherapeutic device of the embodiment illustrated in FIG. 1, showing a controller attached to a base film sheet at a predetermined position.
FIG. 3(b) is a view as seen in the direction of arrow A in FIG. 3(a)
Figure 4:
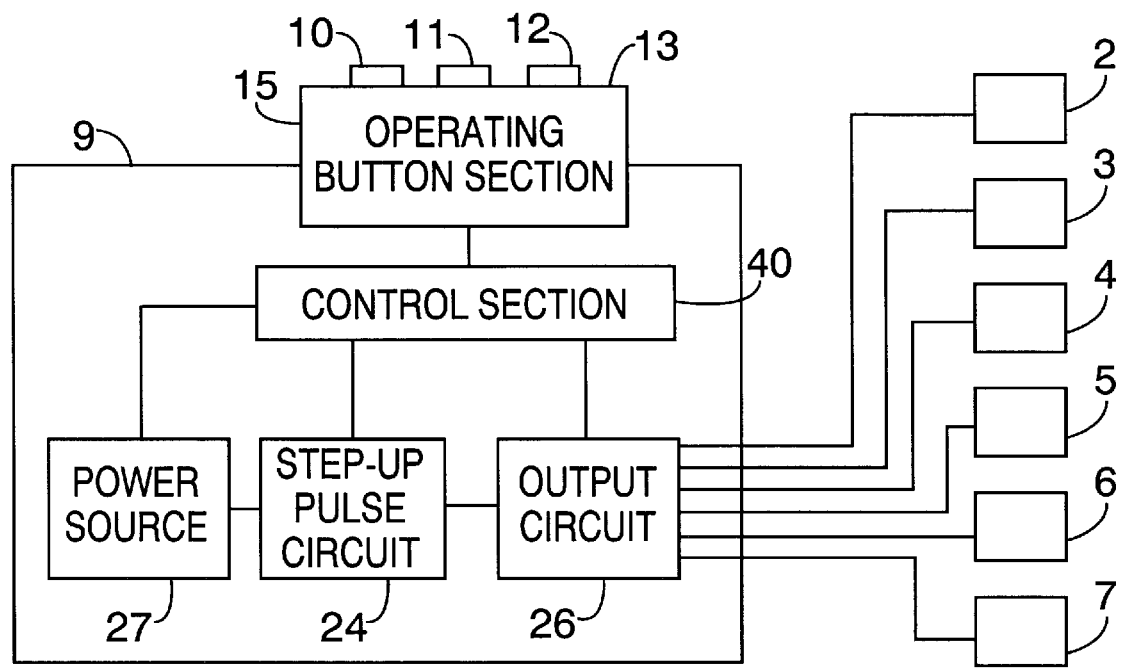
FIG. 4 is a diagram showing a circuit configuration used in the low-frequency electrotherapeutic device of the embodiment illustrated in FIGS. 1 to 3.

FIG. 4 is a diagram showing a circuit configuration in the low-frequency electrotherapeutic device of the embodiment illustrated in FIGS. 1 to 3. The pendant type controller 9 is pendent outside through the pendant cable 8 which is integral with the base film sheet 1. In the interior space of the pendant type controller 9 are disposed a power source 27, a step-up pulse circuit 24, the operating switches 10, 11 and 12, on the operating button section 15 an output circuit 26 including a scanning control function, and a control section (CPU) 40. The power source 27 may include a button battery for example.

The oscillated signal which has been controlled in the control section (CPU) 40 is amplified to an amplitude several times as large as the original amplitude by means of the step-up pulse circuit 24. The step-up pulse circuit 24 then transmits the thus-amplified signal to the output circuit 26, which in turn converts the received signal into pulses having a predetermined width and a frequency, which are controlled by the control section (CPU) 40. The pulses are outputted to the electrodes.

According to the type of stimulation pattern, the output circuit 26 changes the waveform of pulses to be outputted in accordance with a command provided from the control section (CPU) 40 which has been programmed in advance. That is, the output circuit 26 controls the pulse width and amplitude of each pulse and outputs pulses having a group waveform in the shape of, for example, sine wave, square wave, or an exponential wave in which the magnitude increases and decreases exponentially. In accordance with the program stored in the control section (CPU), the output circuit 26 drives a scanning device included in the output circuit and performs an output control based on the combination of the electrodes.

The control section (CPU) 40 successively and selectively supplies output pulses from the output circuit 26 to a plurality of the electrodes 2, 3, 4, 5 and 6 and the central electrode 7. This control is executed by both CPU and program, the details of which will be omitted.

As shown in FIGS. 1 and 2, the operating buttons of the pendant type controller 9 are mounted on the surface thereof. The three buttons 10, 11 and 12 are used to adjust the strength of output, select a stimulation pattern mode and make ON-OFF of the power source.

For example, when the operating button 10 is pushed, the power source turns ON. Upon further depression thereof, a signal is applied to the control section (CPU), so that the supply of the output pulses from the output circuit 26 to a plurality of the electrodes 2, 3, 4, 5, 6 and the central electrode 7 is increased.

When the operating button 12 is pushed, a signal is supplied to the control section (CPU), so that the supply of the output pulses from the output circuit 26 to a plurality of the electrodes 2, 3, 4, 5, 6 and the central electrode 7 is decreased. And upon further depression of the button 12, the power source turns OFF.

When the operating button 11 is pushed once or several times, a signal is fed to the control section (CPU), so that the group waveform of the output pulses supplied from the output circuit 26 to a plurality of the electrodes 2, 3, 4, 5 and 6 or in the central electrode 7 is changed in various ways.

In the low-frequency electrotherapeutic device illustrated in FIGS. 1 to 4 and described above, elements in the output circuit are selected in accordance with commands given from the control section (CPU) in the controller 9, whereby the electrodes 2, 3, 4 and 5 can be designated as different electrodes and the electrode 6 as an indifferent electrode, or likewise one of the electrodes 2, 3, 4 and 5 are designated as an indifferent electrode and the other electrodes as different electrodes. That is, each electrode can be designated as a different electrode or as an indifferent electrode. In the low-frequency electrotherapeutic device of this embodiment, the electrodes 2, 3, 4, 5 and the electrode 6 do not assume a fixed paired structure.

Moreover, in the low-frequency electrotherapeutic device of this embodiment, the supply of an electric current to the different electrodes 2, 3, 4, 5 and 6 can be changed by scanning whenever a predetermined period of time has elapsed, whereby the path of the stimulating current is changed whenever a predetermined period of time has elapsed. For example, the scanning is performed in the order of the different electrodes 2-3-4-5-6-2-3.

In the case where the electrodes 2, 3, 4, 5 and 6 are designated as indifferent electrodes, the path of the stimulating current can be changed by scanning those indifferent electrodes. Besides, since each electrode can be designated as a different electrode or an indifferent electrode, the path of the electric current flowing on the skin of a living body can be selected from various paths, the number of which corresponds to the number of paths connecting the electrodes, i.e., fifteen. As to the combination of electrodes, each electrode can be designated as one of two types of electrodes, i.e., a different electrode and an indifferent electrode, and there are six electrodes in all, each of which can be designated as one of the two types. Therefore, $2^6$ types, i.e., 64 types, of electrode combinations are available. Out of the fifteen types of electric current paths or sixty-four types of electrode combinations, a desired type is selected in accordance with the program in the control section (CPU) incorporated in the controller 9 and it can be changed automatically at predetermined intervals.

Consequently, without frequent change of the affixed position of the base film sheet 1, the positions of the electrodes on the same sheet shift apparently, causing a change of stimulative positions as well.

Figure 5:
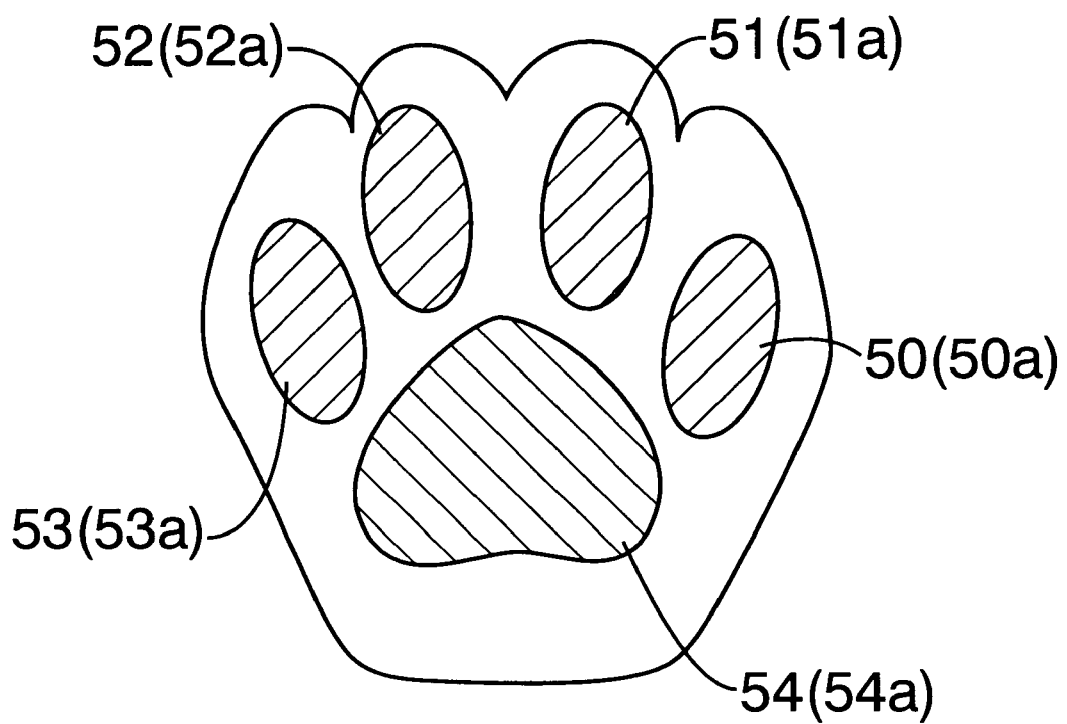
FIG. 5 is a surface view of a low-frequency electrotherapeutic device according to another embodiment of the present invention, showing a portion corresponding to the palm of the hand.

FIG. 5 is a surface view of a low-frequency electrotherapeutic device according to another embodiment of the present invention, showing a portion corresponding to the palm of the hand. The basic construction of this low-frequency electrotherapeutic device is the same as that of the low-frequency electrotherapeutic device of the previous embodiment described above. The low-frequency electrotherapeutic device of this embodiment is different from that of the previous embodiment in that the number of electrodes arranged on the base film sheet is five in all, comprising four fingertip electrodes and one palm electrode. Also in the low-frequency electrotherapeutic device of this embodiment, electrodes 50, 51, 52, 53 and 54 have medicinal adhesive pads 50*a*, 51*a*, 52*a*, 53*a* and 54*a*, respectively, and comprise a non-linear arrangement on the surface a of a base film sheet 1. In other words, the electrodes 50, 52, 52, 53 and 54 comprise an arrangement on a curved line having a curvature smaller than infinity.

Further, also in the low-frequency electrotherapeutic device of the embodiment illustrated in FIG. 5, the electrodes 50, 51, 52 and 53 can be designated as different electrodes and the electrode 54 as an indifferent electrode by means of the control section (CPU) incorporated in the controller 9. Likewise, it is possible to designate one of the electrodes 50, 51, 52 and 53 as an indifferent electrode and the other electrodes as different electrodes. Thus, each electrode can be designated as a different electrode or as an indifferent electrode. A fixed paired structure of a different electrode and an indifferent electrode is not adopted like the previous embodiment.

In the low-frequency electrotherapeutic device of this embodiment, it is possible to change, through scanning, the supply of electric current to the electrodes 50, 51, 52 and 53 designated as different electrodes, whenever a predetermined period of time has elapsed. As a result, the stimulating current path can be changed whenever the predetermined period of time has elapsed. For example, scanning is performed in the order of different electrodes 50-51-52-53-50-51.

In the case where the different electrodes 50, 51, 52 and 53 are designated as indifferent electrodes, the stimulating current path can be changed by scanning those indifferent electrodes. In addition, since it is possible to set each electrode as a different electrode or as an indifferent electrode, the path of the electric current flowing on the skin of a living body can be changed in various paths, whose number corresponds to the number of paths connecting the electrodes, i.e., ten. As to the combination of electrodes, each electrode can be designated as one of two types of electrodes, i.e., a different electrode and an indifferent electrode, and there are five electrodes in all, each of which can be designated as one of the two types. Therefore, $2^5$ types, i.e., 32 types, of electrode combinations are available. Out of the ten types of electric current paths or thirty-two types of electrode combinations, a desired type is selected in accordance with the program in the control section (CPU) incorporated in the controller 9 and it can be changed automatically at predetermined intervals.

A description will be given of various operation patterns in medical treatments performed by using the low-frequency electrotherapeutic devices of the above embodiments.

Figure 6:
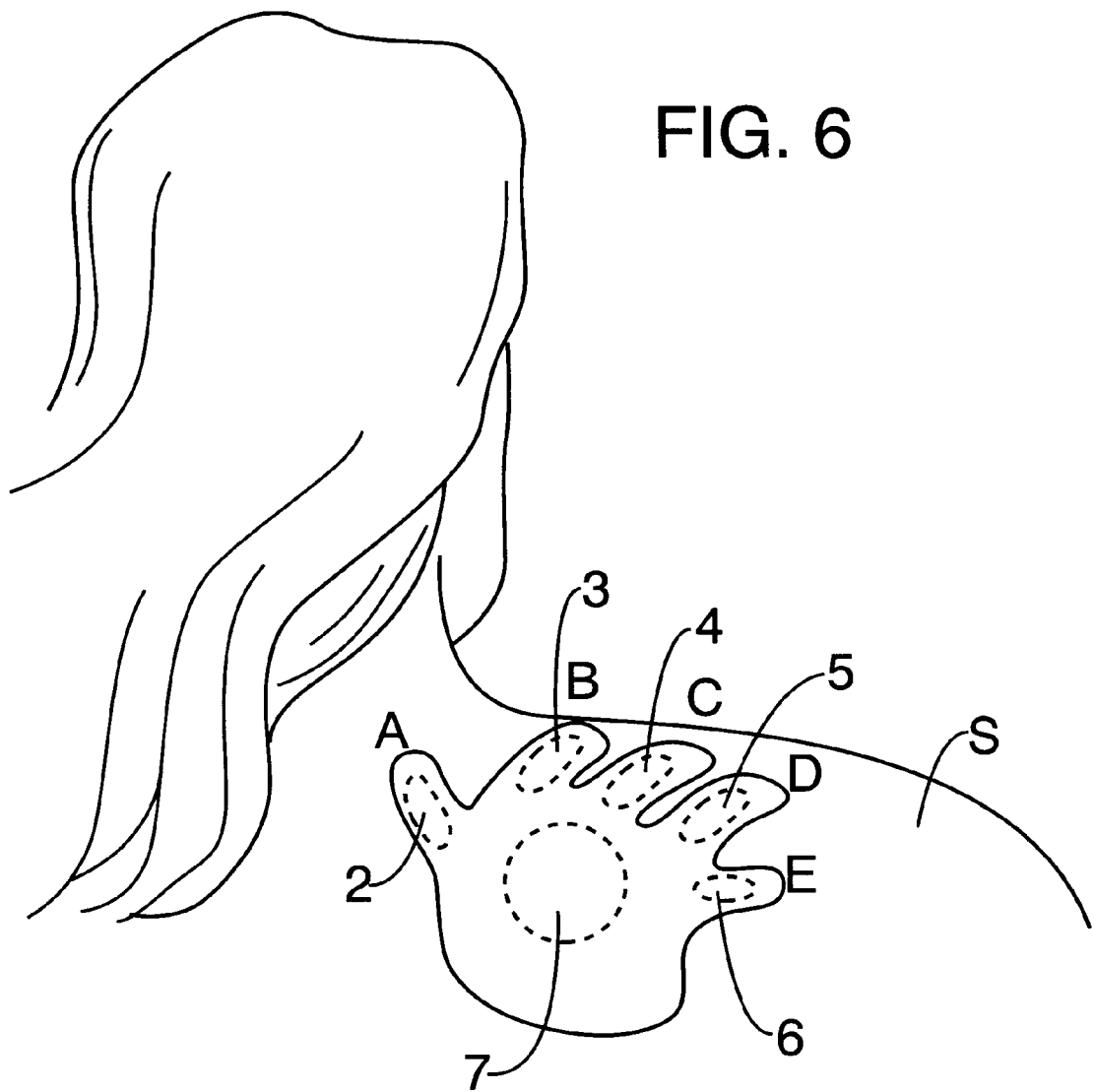
FIG. 6 is a diagram showing the low-frequency electrotherapeutic device of the another embodiment as applied to the shoulder, which device is in the shape of a human hand.
Figure 7:
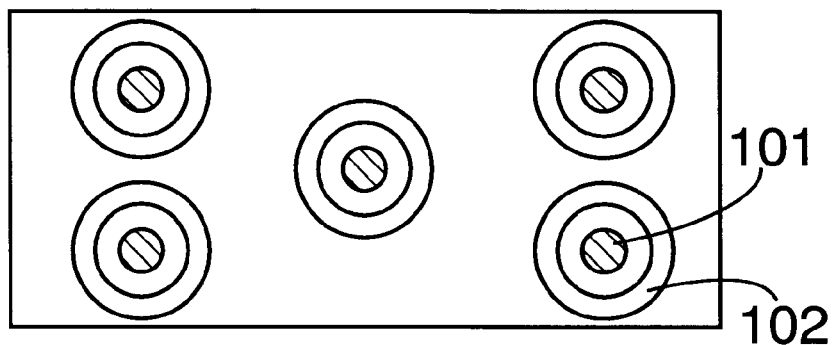
FIG. 7 is an explanatory diagram showing a conventional low-frequency electrotherapeutic device.
Figure 8:
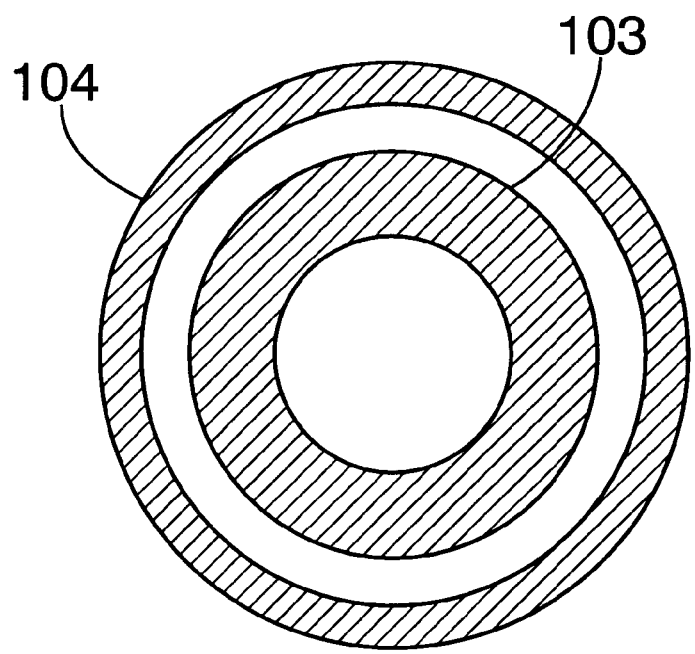
FIG. 8 is an explanatory diagram showing another conventional low-frequency electrotherapeutic device.
Figure 9:
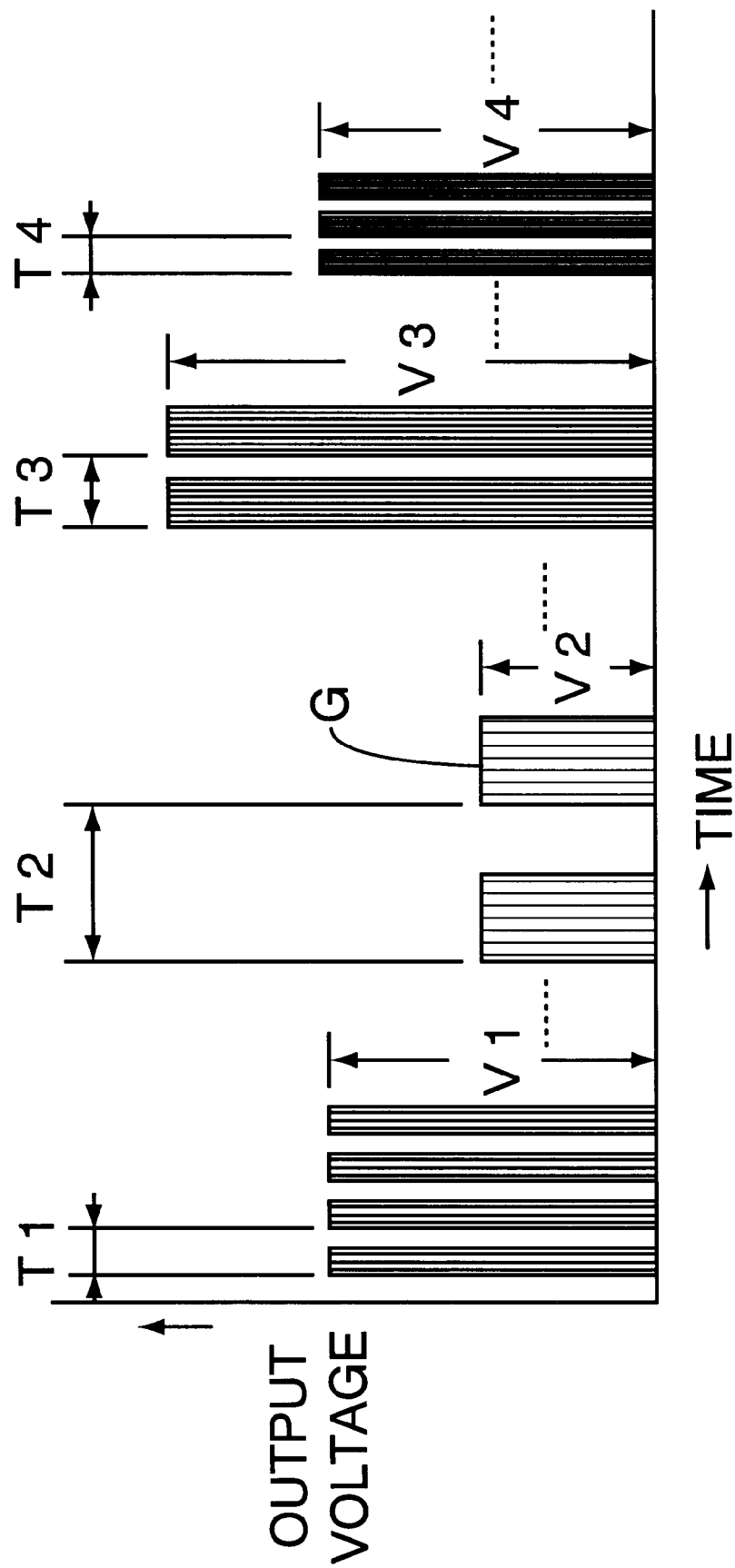
FIG. 9 is a diagram explaining a method of changing the type of stimulation automatically by changing the voltage waveform outputted from a different electrode.
Figure 10:
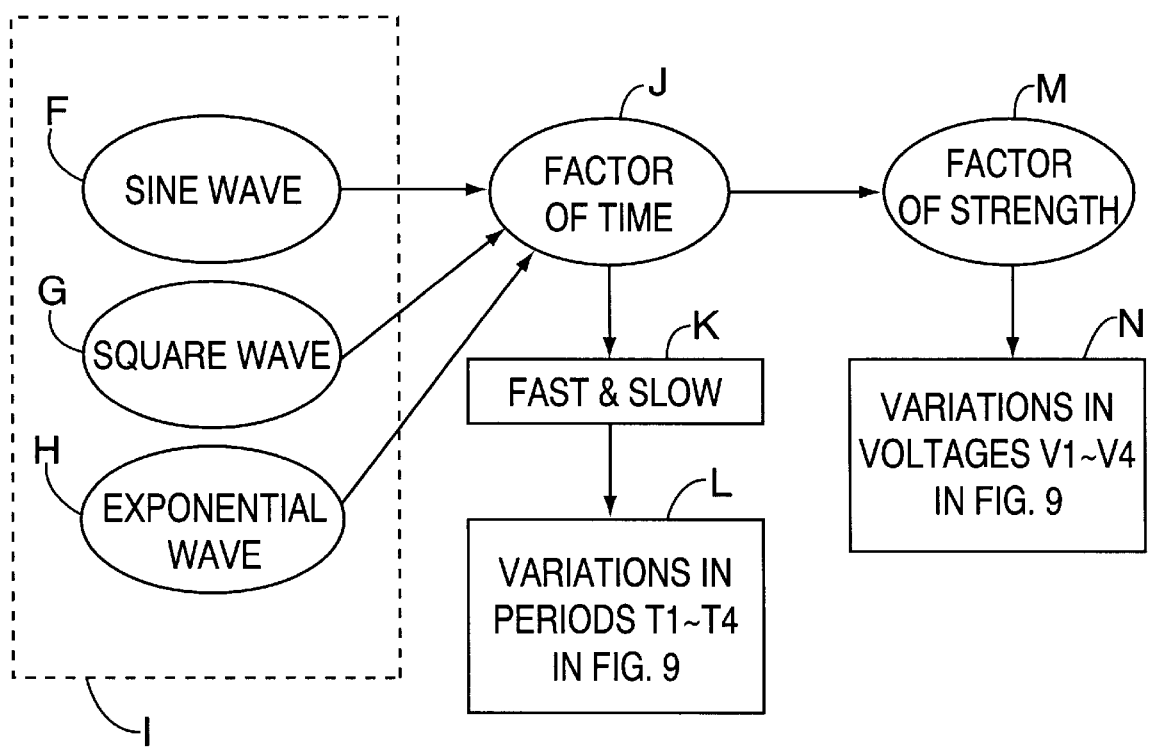
FIG. 10 is an explanatory diagram showing variation in the stimulation pattern of the conventional low-frequency electrotherapeutic device.

(a) "Kneading" Operation Pattern:

FIG. 6 shows a state in which the low-frequency electrotherapeutic device of the embodiment illustrated in FIG. 1, having the shape of the human hand, is applied to the shoulders for example. Usually, when a person "kneads" the shoulder of another person, his or her hand assumes such a position as shown in FIG. 6.

In the "kneading" operation, a force is exerted on the portion A (thumb-electrode 2) and "kneading" operation is performed at the portions B (forefinger-electrode 3), C (middle finger-electrode 4) and D (third finger-electrode 5).

At this time, the portion A (thumb-electrode 2) functions as a fulcrum in the "kneading" operation and thereby permits execution of the "kneading" operation.

Further, when the person performing this operation grasps part of the shoulder and tries to exert a force on fingertips, the portion E (little finger-electrode 6) plays an important role. More particularly, unless the portion E (little finger-electrode 6) also functions as a fulcrum like the portion A (thumb-electrode 2), it is impossible to apply a sufficient force to the fingers of the portions B to D. In the case where a person "kneads" the shoulder of another person, a force is applied to fingertips at the balance mentioned above. The low-frequency electrotherapeutic device takes into account the above fact, and adopts a scanning method for the application of a pressing force, or electric stimulation, successively to the fingertips of the portions B (electrode 3)-C (electrode 4)-D (electrode 5) while applying a moderate pressing force, or electric stimulation to the portions A (thumb-electrode 2) and E (little finger-electrode 6). Thus, the low-frequency electrotherapeutic device can easily perform operations based on human engineering, involving sensing the pressing force at each fingertip of a massaging expert by means of a piezoelectric sensor and application of a voltage with electric stimulation scanning to the fingertips of the portions A to E on the basis of the data obtained by the piezoelectric sensor.

(b) "Rubbing" Operation Pattern:

With the electric stimulation at a fixed limited position performed by the conventional low-frequency medical treatment devices, it is impossible to effect the "rubbing" operation. This is because the "rubbing" operation requires horizontal movements.

On the other hand, the low-frequency electrotherapeutic device according to the embodiment illustrated in FIG. 1 permits positional changes of stimulation because it adopts a free-running electrode system. Thus, the "rubbing" operation is the most favorite operation. More specifically, by scanning the electrodes 2, 3, 4, 5 and 6 in FIG. 1, the patient being treated by this low-frequency electrotherapeutic device can feel a natural "rubbing" massage through an electric stimulation.

In connection with the "rubbing" operation, the structure of the low-frequency electrotherapeutic device allows the "rubbing" operation to be performed in various patterns.

(c) "Tapping" Operation Pattern:

The "tapping" operation in the conventional low-frequency electrotherapeutic devices is conducted at a single position because a different electrode and an indifferent electrode are fixed in a pair.

On the other hand, the low-frequency electrotherapeutic device of the present embodiment can adopt a method wherein the electrode 7 in FIG. 1 which electrode corresponds to the palm of the hand is designated as a different electrode of a large size, while the fingertip electrodes 2 to 6 are designated as indifferent electrodes, and those indifferent electrodes are scanned. According to this method, even when "tapping" stimulation is generated continuously in the electrode 7 designated as a different electrode, the stimulating current path is changed by scanning the fingertip electrodes 2 to 6 designated as indifferent electrodes, resulting in that it becomes possible to prevent the accumulation of an electric charge in a living body. Thus, it can be expected that the "tapping" effect obtained by using the low-frequency electrotherapeutic device will last long continuously without attenuation.

In connection with the above operation, it is possible to designate the electrode 7 as an indifferent electrode and the fingertip electrodes 2 to 6 as different electrodes and the position of stimulation provided by the electrodes 2 to 6 is changed whenever a predetermined period of time has elapsed. By the addition of this operation pattern, the "tapping" stimulation by the electrode 7 is followed by a soft "tapping" stimulation involving a positional shift around the electrode 7, whereby there is obtained a "tapping" sense which is more natural and closer to the human motion than the monotonous "tapping" stimulation at a limited position. This operation is effective also in preventing the tolerance of the nervous system.

Although the above operation patterns have been described with respect to the low-frequency electrotherapeutic device of the embodiment illustrated in FIG. 1, a low-frequency medical treatment using the same operation pattern can be performed by the low-frequency electrotherapeutic device of the embodiment illustrated in FIG. 5.

What is claimed is:

1. A low-frequency electrotherapeutic device, comprising:
   a step-up pulse circuit;
   a control section for controlling said step-up pulse circuit;
   a power source for supplying electric power to both said step-up pulse circuit and said control section;
   an output circuit connected to said step-up pulse circuit, said output circuit being controlled by said control section; and
   three or more electrodes connected to said output circuit, wherein each of said electrodes is freely designated as a different electrode or as an indifferent electrode,
      wherein the control section is adapted to control electrical stimulation carried out by the electrodes to have a flexible temporal pattern causing irregular and unexpected changes, and
      wherein the electrical stimulation carried out by the electrodes provides a low frequency, electrotherapeutic effect.

2. A low-frequency electrotherapeutic device according to claim 1, wherein a switching means is further provided to change an electric current path between a different electrode (s) and an indifferent electrode(s).

3. The low-frequency electrotherapeutic device of claim 1 wherein the electrical stimulation carried out by the electrodes provides a muscle massage.

4. A low-frequency electrotherapeutic device according to claim 1, wherein a switching means is further provided to change an electric current path between a different electrode (s) and an indifferent electrode(s) and said output circuit drives a scanning device to scan a plurality of the electrodes serving as different electrodes or indifferent electrodes.

5. A low-frequency electrotherapeutic device according to claim 4, wherein a different electrode(s) and an indifferent electrode(s) are independently designated by said control section.

6. A low-frequency electrotherapeutic device according to claim 5, wherein said electrodes are arranged in a single sheet and are disposed at positions closely similar to the positions of the human fingers and palm, based on human engineering.

7. A low-frequency electrotherapeutic device, comprising:
   a step-up pulse circuit;
   a control section for controlling said step-up pulse circuit;
   a power source for supplying electric power to both said step-up pulse circuit and said control section;
   an output circuit connected to said step-up pulse circuit, said output circuit being controlled by said control section; and
   three or more electrodes connected to said output circuit, wherein each of said electrodes is freely designated as a different electrode or as an indifferent electrode, and the thus-designated different and indifferent electrodes do not form a fixed pair arrangement,
      wherein the control section is adapted to control electrical stimulation carried out by the electrodes to have a flexible temporal pattern causing irregular and unexpected changes, and
      wherein the electrical stimulation carried out by the electrodes provides a low frequency, electrotherapeutic effect.

8. The low-frequency electrotherapeutic device of claim 7 wherein the electrical stimulation carried out by the electrodes provides a muscle massage.

9. A low-frequency electrotherapeutic device, comprising:
   a step-up pulse circuit;
   a control section for controlling said step-up pulse circuit;
   a power source for supplying electric power to both said step-up pulse circuit and said control section;
   an output circuit connected to said step-up pulse circuit, said output circuit being controlled by said control section; and
   three or more electrodes connected to said output circuit, each of said electrodes is freely designated as a different electrode or as an indifferent electrode, and the thus-designated different and indifferent electrodes form a paired arrangement, and a desired combination of different and indifferent electrodes is formed,
      wherein the control section is adapted to control electrical stimulation carried out by the electrodes to have a flexible temporal pattern causing irregular and unexpected changes, and
      wherein the electrical stimulation carried out by the electrodes provides a low frequency, electrotherapeutic effect.

10. A low-frequency electrotherapeutic device according to claim 9, wherein the control section includes means for independently controlling said plurality of electrodes through the operation of said output circuit.

11. A low-frequency electrotherapeutic device according to claim 9, wherein said three or more electrodes comprise a non-linear arrangement.

12. A low-frequency electrotherapeutic device according to claim 9, wherein said three or more electrodes comprise an arrangement along a curved line whose curvature is smaller than infinity.

13. The low-frequency electrotherapeutic device of claim 9 wherein the electrical stimulation carried out by the electrodes provides a muscle massage.

14. A low-frequency electrotherapeutic device, comprising:
   a step-up pulse circuit;
   a control section (CPU) for controlling said step-up pulse circuit;
   a power source for supplying electric power to both said step-up pulse circuit and said control section (CPU);
   an output circuit connected to said step-up pulse circuit, said output circuit being controlled by said control section (CPU);
   three or more electrodes connected to said output circuit, wherein each of said electrodes is freely designated as a different electrode or as an indifferent electrode, wherein said electrodes are arranged on a single sheet and are disposed at positions closely similar to positions of the human fingers and palm, based on human engineering; and
   a switching means to change an electric current path between a different electrode(s) and an indifferent electrode(s), wherein said output circuit drives a scanning device to scan a plurality of electrodes serving as different electrodes or indifferent electrodes, said different electrodes and said indifferent electrodes being independently designated by said control section.

15. A low-frequency electrotherapeutic device according to claim 14, wherein said electrodes are arranged on each of the front and back surfaces of said single sheet.

16. A low-frequency electrotherapeutic device according to claim 15, wherein said single sheet has cuts so as to easily fit a curved surface of a living body when attached to the living body.

17. A low-frequency electrotherapeutic device according to claim 16, wherein an end portion of said single sheet is extended, and said control section is connected to the extended portion, said electrodes being controlled by said control section.

18. A low-frequency electrotherapeutic device according to claim 17, wherein said control section is detachably attached to said single sheet to be located at a predetermined position thereof, by using a magic tape provided on said single sheet.

19. A low-frequency electrotherapeutic device, comprising:

a step-up pulse circuit;

a control section (CPU) for controlling said step-up pulse circuit;

a power source for supplying electric power to both said step-up pulse circuit and said control section (CPU);

an output circuit connected to said step-up pulse circuit, said output circuit being controlled by said control section (CPU);

three or more electrodes connected to said output circuit, each of said electrodes being freely designated as a different electrode or as an indifferent electrode and disposed at positions closely similar to positions of the human fingers and palm, based on human engineering;

a single sheet having cuts so as to easily fit a curved surface of a living body when attached to the living body and an end portion of said sheet is extended and said control section is connected to the extended portion and is detachably attached to said single sheet to be located at a predetermined position thereof, by using a magic tape provided on said single sheet wherein said electrodes are arranged on each of the front and back surfaces of said single sheet, and wherein each said electrode has, on the surface thereof, an adhesive pad having a bonding surface which has stickiness for the skin; and a switching means to change an electric current path between a different electrode(s) and an indifferent electrode(s), wherein said output circuit drives a scanning device to scan said plurality of electrodes serving as different electrodes or indifferent electrodes, said different electrodes and said indifferent electrodes being independently designated and controlled by said control section.

20. A low-frequency electrotherapeutic device according to claim 19, wherein said adhesive pad is impregnated with medicine.

* * * * *